May 19, 1964 G. H. FUJII Plant Pat. 2,404
VERBENA PERUVIANA PLANT
Filed Dec. 7, 1962
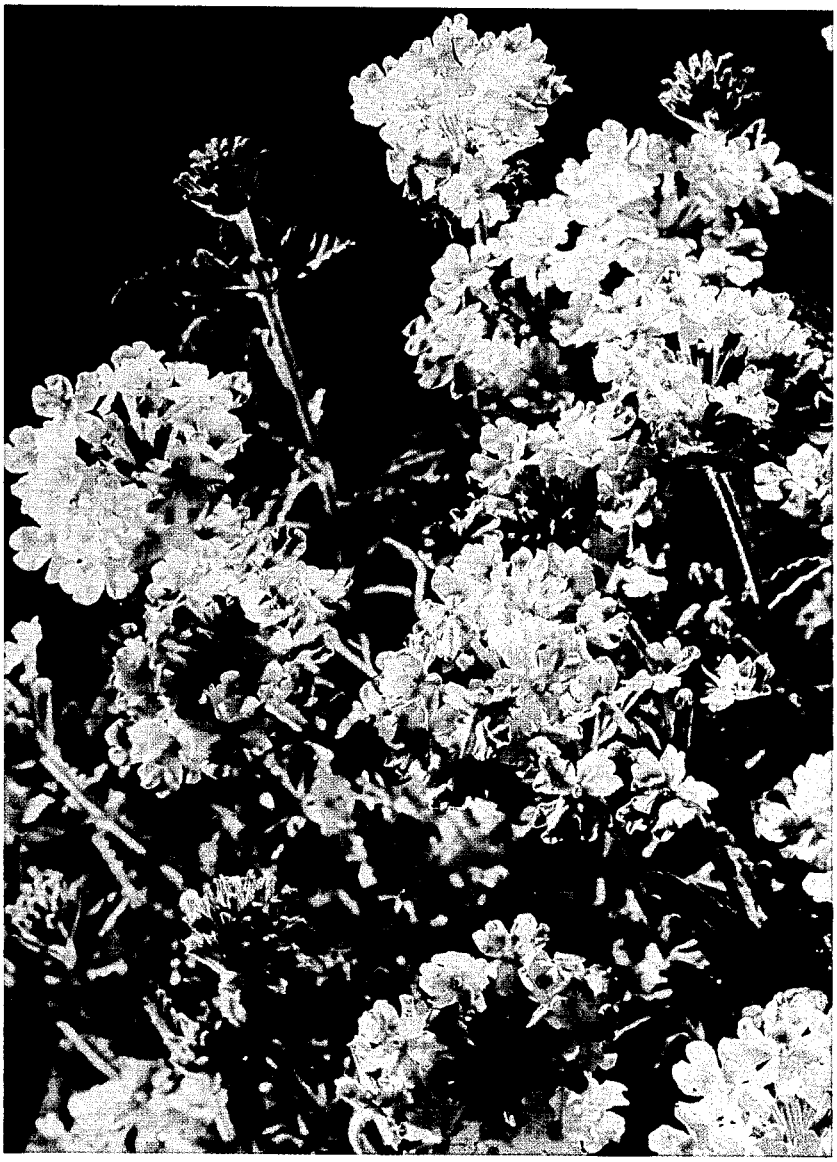
INVENTOR
GEORGE H. FUJII
BY J. F. Cuneo
ATTORNEY United States Patent Office Plant Pat. 2,404
Patented May 19, 1964

2,404
*VERBENA PERUVIANA* PLANT
George H. Fujii, 16711 S. Berendo, Gardena, Calif.
Filed Dec. 7, 1962, Ser. No. 243,171
1 Claim. (Cl. Plt.—87)

This invention makes available at new and distinct variety of *Verbena peruviana* plant of the prostrate type.

The new and distinct variety is characterized by its unique white blooms that are borne in rather large clusters on a long stiff stem; and by its rather thick leaves that are a medium bright green. The plant is of the ground cover type and its branches and leaves are classed as prostrate and spreading. The new variety exhibits a vigorous and hardy growth.

The new and distinct variety of *Verbena peruviana* was discovered be me as a sport growing in a cultivated bed of ordinary unpatented variety of *Verbena peruviana* that is situated on my property located at 564 E. 165th Street, in the city of Gardena, county of Los Angeles, State of California. The sport was discovered by me in March 1959.

The new variety has been reproduced asexually at 564 E. 165th Street, Gardena, California, from cuttings and all of the descendants of this plant have exhibited the distinguishing characteristics of the new and distinct variety, thereby establishing that the strain is true. A large number of cuttings have been made since the new variety was discovered. This new variety cannot be reproduced true from seed.

The accompanying illustration in full color, shows typical specimens of the flower and leaves. The colors in the illustration are as correct as it is possible to reproduce them by this type of illustration.

A detailed description of the new variety of *Verbena peruviana* follows. To assist and facilitate identification of the important colors mentioned in this specification, the nomenclature adopted by the British Horticultural Colour Charts has been followed.

*Flowers*

Locality where grown and observed: Gardena, California.

Flowers borne: Clusters of individual flowers are borne on stiff erect stems, the length of the stem varying from four to eight inches.

*Number of individual flowers.*—The flowers are generally in clusters of 17 to 19 and these are borne on a single stem.

*Size of clusters.*—The flowers are arranged in the form of a rough circle that is from 1¾″ to 2″ in diameter.

Individual flowers:

*Size.*—Each individual flower has generally five petals and the flowers are from ½″ to a maximum of ⅝″ in diameter; the small size gives the cluster a dainty appearance.

*Color.*—The flowers are white both outside and inside. The center of each flower has a pale yellow eye.

*The Plant*

Habit: The plant is of the prostrate type. The plant exhibits a vigorous growth and makes an excellent ground cover.

Blooming habit: The plant blooms abundantly from February to November in the area in which it was observed in southern California. The blooming period is extended into the late fall if the weather remains warm, as it sometimes will in southern California.

Leaves:

*Shape.*—Leaves are ovate or oblong triangular and have a substantially cuneate base that is decurrent into a rather short petiole, the petiole in some leaves is very short; divisions are pinnatified giving a serrated effect to the margin of the leaves, the leaves have a tendency to be revolute at the margins.

*Texture.*—The leaves are relatively thick, veiny and rugose, the lower portion of the leaves being covered with short stiff hairs that are particularly noticeable on the veins.

*Borne on stem.*—The leaves are generally opposite. Each opposite pair of leaves is positioned on the stem at substantially right angles to the adjoining pair of leaves; there is considerable distance between pairs.

*Size.*—Mature leaves vary from ⅞″ to 1⅛″ in length; the leaves are approximately from ⅝″ to ¾″ in width at the widest portion of the leaf near the base and the portion of the leaf adjoining the widest part will vary from ½″ to ⅜″ in width, this narrower portion tapering to a narrow point at the outer end of the leaf.

*Color.*—Upper side—Parsley Green oo962/1. Lower side—Parsley Green oo962/3. The leaves appear to maintain their bright green color even after prolonged exposure to bright sunlight.

Branches: The brances remain close to the ground and extend in all directions from the central portion of the plant. The length of the stems is from 5″ to 7″.

Rooting: The plant is self rooting.

Aroma: The blooms of the plant have no appreciable aroma and the foliage has no distinctive aroma.

I claim:

A new and distinct variety of Verbena plant substantially as illustrated and described, characterized by its all white individual flowers in clusters of many flowers borne on a stiff substantially erect stem, and by its medium sized bright green leaves borne opposite each other and widely spaced on the stems, and by its vigorous growth.

No references cited.